United States Patent [19]

Arimond

[11] Patent Number: 4,624,661
[45] Date of Patent: Nov. 25, 1986

[54] DRUG DISPENSING SYSTEM

[75] Inventor: Timothy V. Arimond, Minneapolis, Minn.

[73] Assignee: Surgidev Corp., Santa Barbara, Calif.

[21] Appl. No.: 730,434

[22] Filed: May 6, 1985

Related U.S. Application Data

[63] Continuation of Ser. No. 442,039, Nov. 16, 1982, abandoned.

[51] Int. Cl.$^4$ ............................................. A61M 37/00
[52] U.S. Cl. .............................. 604/151; 128/DIG. 12
[58] Field of Search ................ 128/DIG. 12–DIG. 13; 604/67, 151

[56] References Cited

U.S. PATENT DOCUMENTS

| | | | |
|---|---|---|---|
| 4,270,532 | 6/1981 | Franctzki et al. | 604/151 |
| 4,296,756 | 10/1981 | Dunning et al. | 128/904 X |
| 4,308,866 | 1/1982 | Jelliffe et al. | 604/67 X |
| 4,373,527 | 2/1983 | Fischell | 128/DIG. 12 X |
| 4,405,318 | 9/1983 | Whitney et al. | 128/DIG. 12 X |
| 4,475,901 | 10/1984 | Kraegen et al. | 128/419 P X |

OTHER PUBLICATIONS

Clemens, A. H. et al., "The Development of Biostator, A Glucose Controlled Insulin Infusion System (GCIIS)", Freiburg Workshop, late 1970's.

Primary Examiner—Kyle L. Howell
Assistant Examiner—Francis J. Jaworski
Attorney, Agent, or Firm—Hugh D. Jaeger

[57] ABSTRACT

Drug dispensing system for dispensing of drugs from a reservoir or external reservoir such as a standard I.V. bag through a drug dispenser according to a preselected algorithm controlling a motor where a CPU pumps the drug. An external controller for the drug dispenser stores a plurality of parameters including a patient number, name, drug dispenser number, date, time, drug, an algorithms for dispensing the drug including dosage levels and frequency of dosage where the algorithm is stored in the external controller and the program is subsequently stored in the CPU of the drug dispenser for subsequent controlling of the motor driving the pump for dispensing of the drug. The external controller also includes an LCD display for medical personnel interaction and a printer for hard copy storage of the selected algorithm and other information as programmed into the external controller by a keyboard. A flexible cord connects the external controller to a drug dispenser for programming the CPU for an algorithm for dispensing a drug by the drug dispenser.

27 Claims, 7 Drawing Figures

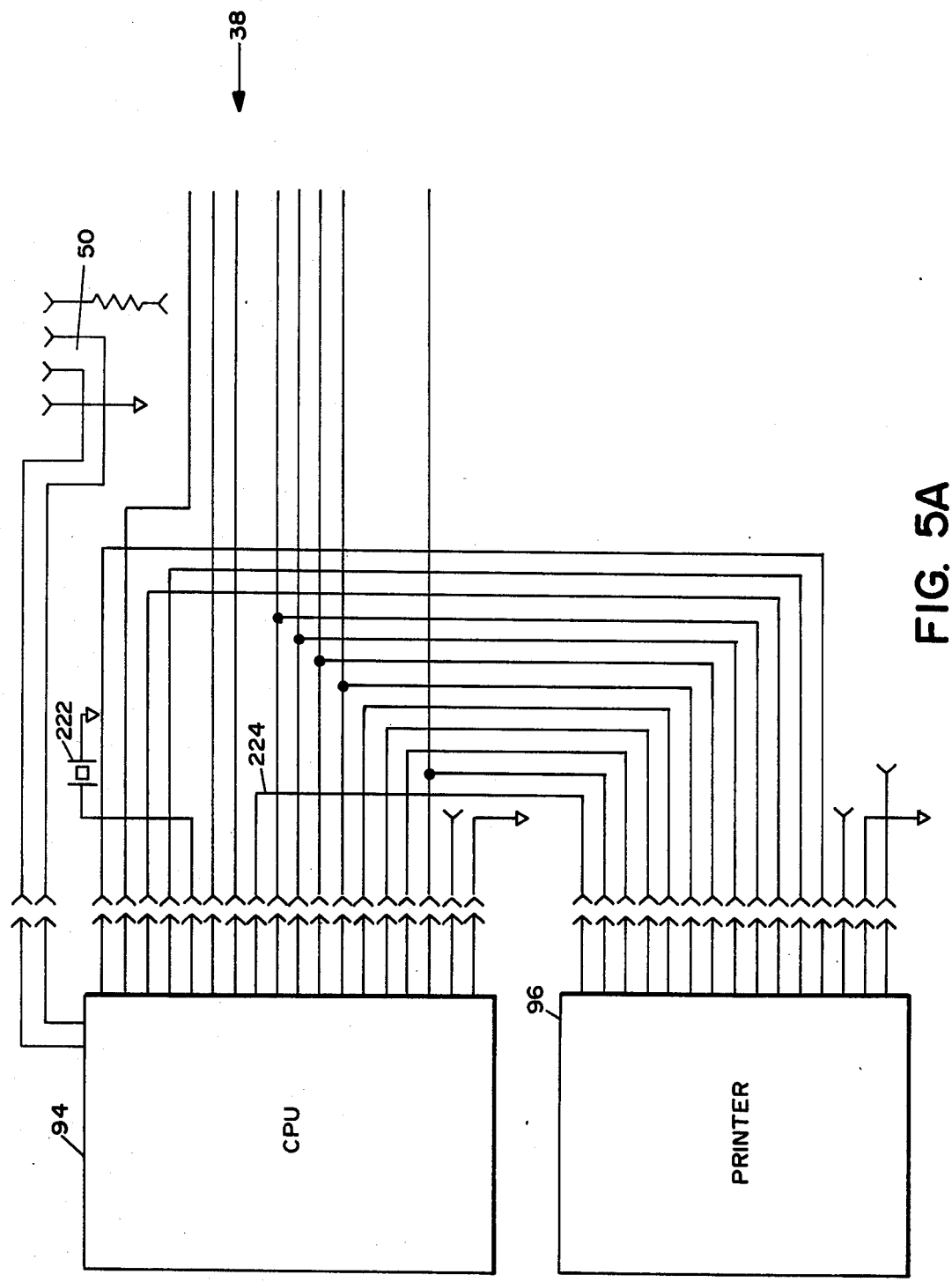

DRUG DISPENSING SYSTEM

This application is a continuation of application Ser. No. 442,039, filed 11/16/82 and now abandoned.

BACKGROUND OF THE INVENTION

1. Field of the Invention

Present invention relates to electrical surgical programmable drug dispensing systems and, more particularly, pertains to a programmable drug dispensing system which can utilize preselected algorithms as locally stored or can also process algorithms stored in other computers for dispensing of drugs by the drug dispensing system.

2. Description of the Prior Art

Prior art drug dispensing devices and systems are currently in the infancy of development.

The prior art dispensing systems lack an accurate delivery at constant flow rate of drugs. The controlled repeatability of the prior art systems has been minimal, and a particular cause of concern has been leakage of the drug through the pumps. Very few of the prior art systems have utilized a self-contained reservoir.

Also, the prior art drug dispensing systems have not allowed for programmability and this has not been particularly useful from a practical bedside or implantable standpoint.

Further, the prior art drug dispensing systems have not utilized a controller that prints out the paramaters such as the patient, date, time, drug, dosage levels and frequency of dosage.

Finally, the prior art systems have not utilized a plurality of specific algorithms nor have the systems been adaptable to the currently generated computer system storing numerous algorithms for the numerous drugs available through prescription.

The present invention overcomes the disadvantages of the prior art by providing a drug dispensing system including a drug dispenser and an external controller for the drug dispenser. The drug dispenser utilizes a CPU controlled pump motor for repeated and accurate dispensing of drugs at predetermined levels and frequency. The drug dispenser CPU is programmed by the external controller or through the external controller from a third computer storage of drug dispensing algorithms. The drug dispenser is reuseable, can dispense critical drugs in minute quantities or noncritical drugs in large volume, and is particularly designated for burn victims, cancer patients, diabetic stabilization, metabolic rate testing, and heart attack victims.

SUMMARY OF THE INVENTION

The general purpose of the present invention is to provide an accurate drug dispensing system for dispensing drugs to an individual in critical and non-critical medical care situations. The drug dispensing system can be utilized by medical personnel with even limited experience in its use, such as registered nurses, physicians, surgeons and the like. The dispensed drug is dispensed at controlled dosage over a controlled time period according to an algorithm which programs the drug dispenser through an external controller for the drug dispenser. The drug dispensing system can also be utilized with computing systems having stored algorithms for drugs including predetermined dosage as well as frequency of dosage schedules.

According to one embodiment of the present invention, there is provided a drug dispensing system including a drug dispenser having a source of power and internal rechargeable battery supply, a real-time clock, a CPU and RAM, an address latch, a ROM, an I/O port, a buffer connected to LED's indicators and an acoustical alert, a motor buffer between the I/O port and a motor for driving a pump, a pump detector line between the motor and the CPU and RAM, and the pump pumping drugs from either an internal reservoir or an external reservoir such as an I.V. or the like bottle to the patient, the pump including a stepper motor and replaceable tubing, the external controller including a CPU for storing a plurality of drug dispensing algorithms for particular drugs, dosage levels, and frequency of dosage, a key pad and key pad interface connected to the CPU, a printer and printer interface connected to the CPU for outputting hard copy as well as an LCD display and interface for displaying copy of patient's number, patient's name, drug dispenser number, date, time, drug, selective algorithm, dosage levels, frequency of dosage, expected response, and other parameters as inputted or outputted through the algorithm, and an I/O port for inputting as well as outputting drug dispensing algorithms stored in a separate computer system which is capable of interconnecting and interfacing with the external controller for the drug dispenser whereby the drug dispensing system dispenses predetermined dosage levels of a drug at a predetermined frequency according to a program stored in the drug dispenser CPU, that program inputted through an algorithm of the external controller or as inputted to the external controller, and monitoring with indicators the status of the drug dispenser. LED indicators on the drug dispenser indicate a power on condition, a drug dispensing program in action, an alarm indicating either loss of power or low battery, and an indicator indicating low drug. An acoustical alert sounds for all indicating positions such as low battery, loss of power, flow failure, or the like.

One significant aspect and feature of the present invention is a drug dispensing system which has low power consumption and also low current drain in a standby condition. This is particularly important in applications where AC power is not readily available or in the loss of AC power. A nicad battery provides a rechargeable energy source while a lithium backup battery provides emergency power as demanded. The low current drain particularly results from utilization of CMOS circuitry which is important in field or remote considerations in medical treatment.

Another significant aspect and feature of the present invention is a broad range of dispensing critical drugs in minute quantities to non-critical drugs in large volumes or in between as required. The drug dispensing system utilizing a stepper motor pump is able to dispense the drugs as required at a particular dosage over a particular frequency of time in real-time situations.

A further significant aspect and feature of the present invention is a reuseable drug dispenser system including the drug dispenser. The particular pump provides for replacement of the tubing about which rollers propel the drug. The tubing connects between the individual to the drug reservoir which can be either internal to the drug dispenser or external and the internal reservoir also being replaceable as required. This provides for the sterility of the system as well as non-contamination during dispensing. Any length of tubing can be utilized between the drug dispenser and the patient.

An additional significant aspect and feature of the present invention is a drug dispenser dispensing drugs for burn victims, diabetic individuals or for diabetic stabilization, unconscious persons, metabolic rate testing, cancer patients and heart attack victims.

Having thus described one embodiment of the present invention, it is the principal object hereof to provide a drug dispensing system including a drug dispenser, an external controller for the drug dispenser, and a drug which is dispensed through the drug dispenser according to an algorithm programmed into the drug dispenser by an external controller.

One object of the present invention is to provide a drug dispenser which dispenses drugs from minute quantities to large volumes as required. The frequency of dosage and dosage level is programmed into the drug dispenser CPU which controls the execution of the stepper motor driving the pump.

Another object of the present invention is a drug dispensing system which utilizes a printer for keeping track of relevant information including the patient number and name, drug dispenser number, date, time, drug, dosage level, frequency of dosage, and other information as required and as requested through an algorithm or programmed in through the key pad.

A further object of the present invention is to provide a drug dispenser with alert digital indicators and auditory indicators providing self diagnostics of operation.

BRIEF DESCRIPTION OF THE DRAWINGS

Other objects and many of the attendant advantages of this invention will be readily appreciated as the same becomes better understood by reference to the following detailed description when considered in connection with the accompanying drawings, in which like reference numerals designate like parts throughout the figures thereof and wherein.

DESCRIPTION OF PREFERRED EMBODIMENTS

Figure 1:
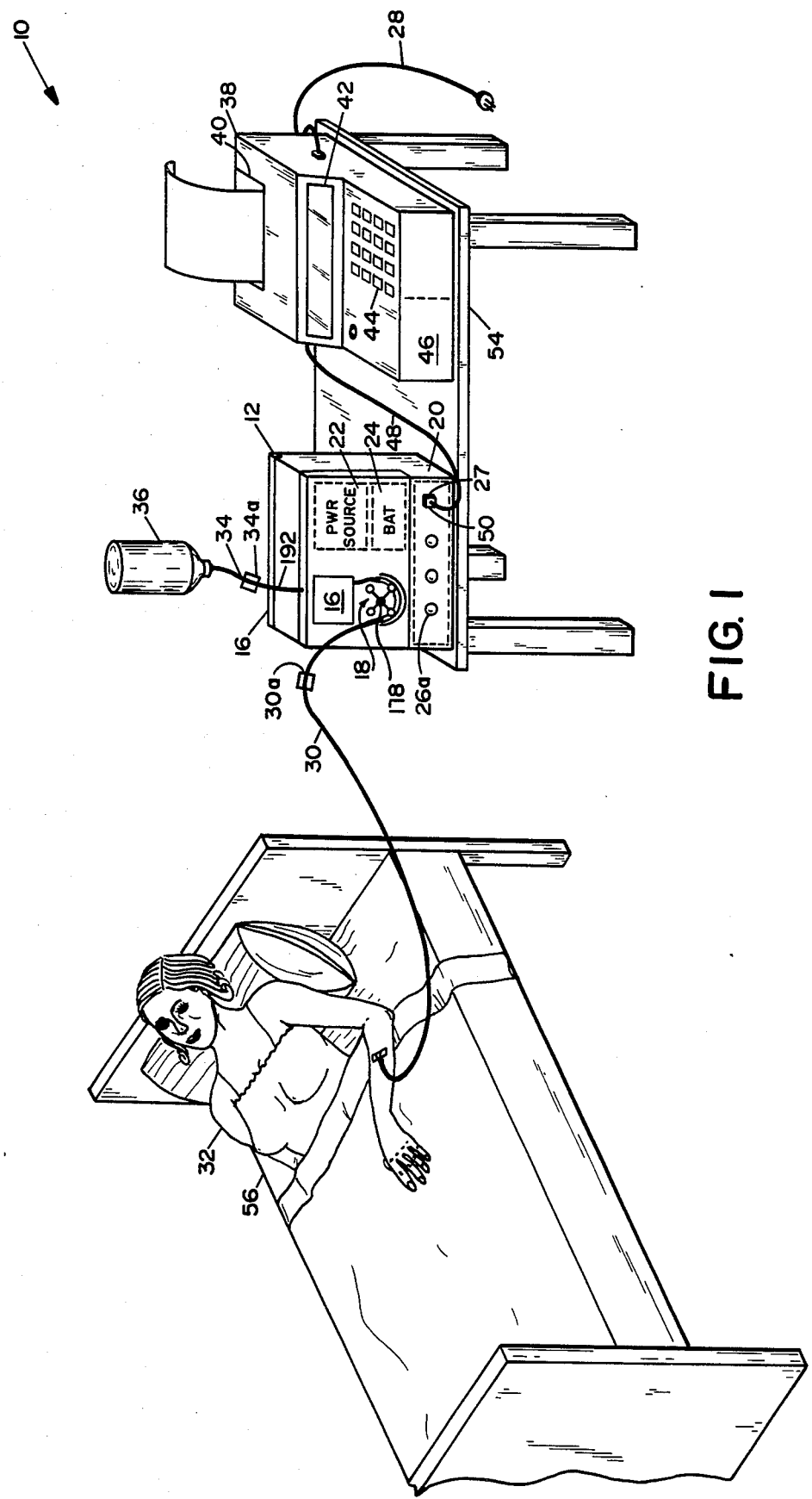
FIG. 1 illustrates a perspective view of a drug dispensing system including a drug dispenser connected to a patient, and an external controller for the drug dispenser.

FIG. 1 illustrates a perspective view of a drug dispensing system 10, the present invention, including a drug dispenser 12 connected to a patient as later described, and an external controller 38 for the drug dispenser 12. The drug dispenser housing 12 includes a drug reservoir 16, a motor pump assembly 18, electronics 20 as later described in FIGS. 2, 4A and 4B, a first power source 22, a backup power source 24, and a plurality of indicator lights 26a-26n. A tube 30 connects between the drug pump 18 and a patient 32. An external tube 34 can connect to an external reservoir such as an I.V. bag or bottle of drugs. Socket 27 receives input signals from external controller 38. Leur locks 30a and 34a are provided on tubes 30 and 34 respectively. The drug dispenser 12 can be the size of a pack of cigarettes or the like.

The external controller 38 for the drug dispenser includes an electrostatic printer 40, an LCD display 42, a key pad 44 for inputting patient information and algorithm selection, internal electronics 46, a flexible cord 48 with a plug 50 for connecting to the drug dispenser 12. A housing 52 supports elements 40–50. A table 54 can support the drug dispenser 12 as well as the external controller 38 adjacent to the bed 56, or the drug dispenser can be worn on the belt of an ambulatory patient. A plurality of drug dispensing algorithms 58a–58n is stored in the electronics 46 of the external controller 38, as later described in detail in FIGS. 3 and 5A–5D. A line cord 28 provides power to the external controller 38.

Figure 2:
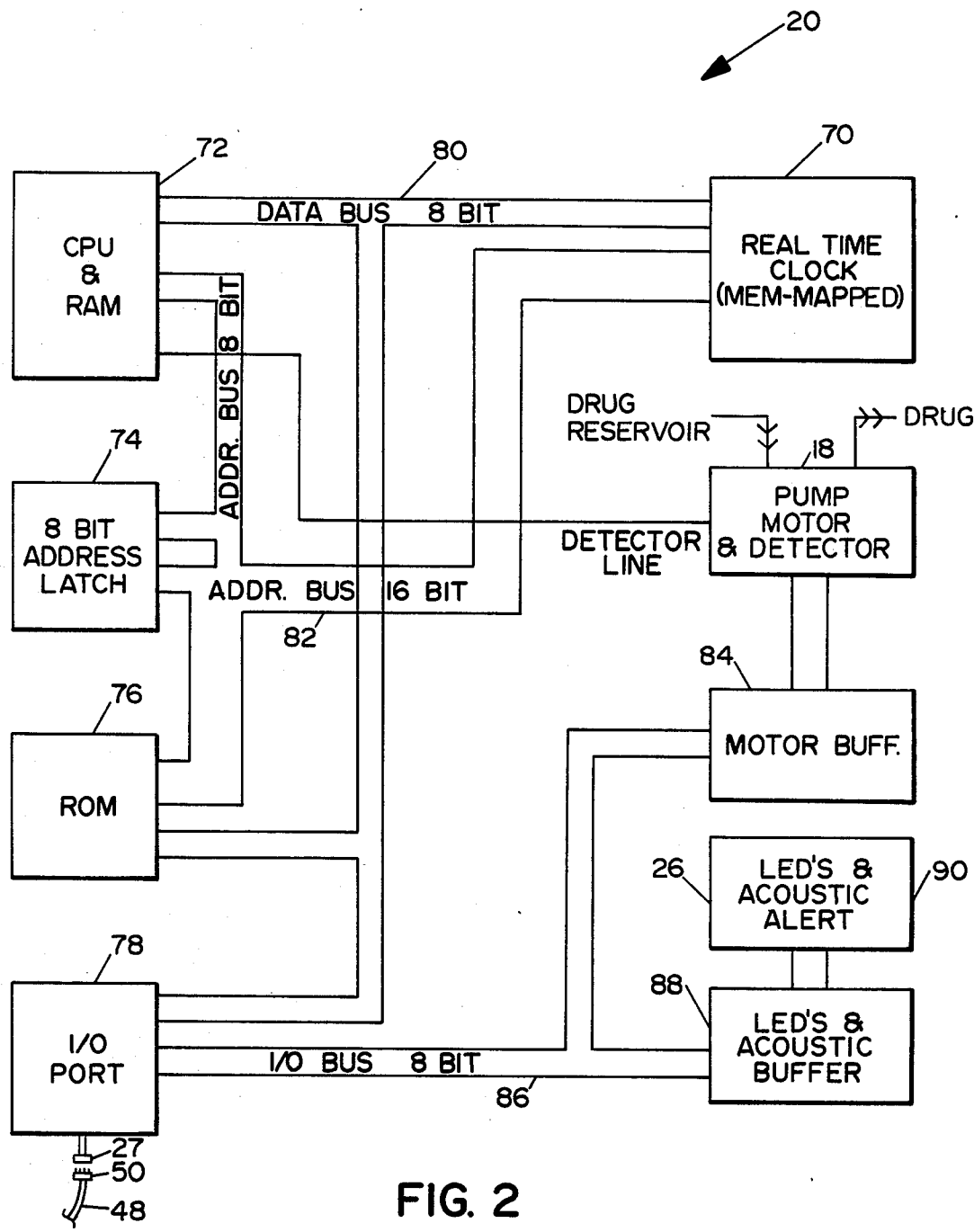
FIG. 2 illustrates a block diagram of the drug dispenser.

FIG. 2 illustrates a block diagram of the drug dispenser 12. The drug dispenser 12 includes a real-time memory mapped clock 70, a CPU and RAM 72, an address latch 74, a ROM 76, an I/O port 78, the elements connected by a data bus 80 and an address bus 82. A motor buffer 84 connects to the pump motor 18 through an I/O bus 86 to the I/O port 78. A buffer 88 connects to the I/O port 78 through the buss 86 and connects to the LEDs 26 and acoustic alert 90. Address buss 82 connects to 70–76.

Figure 3:
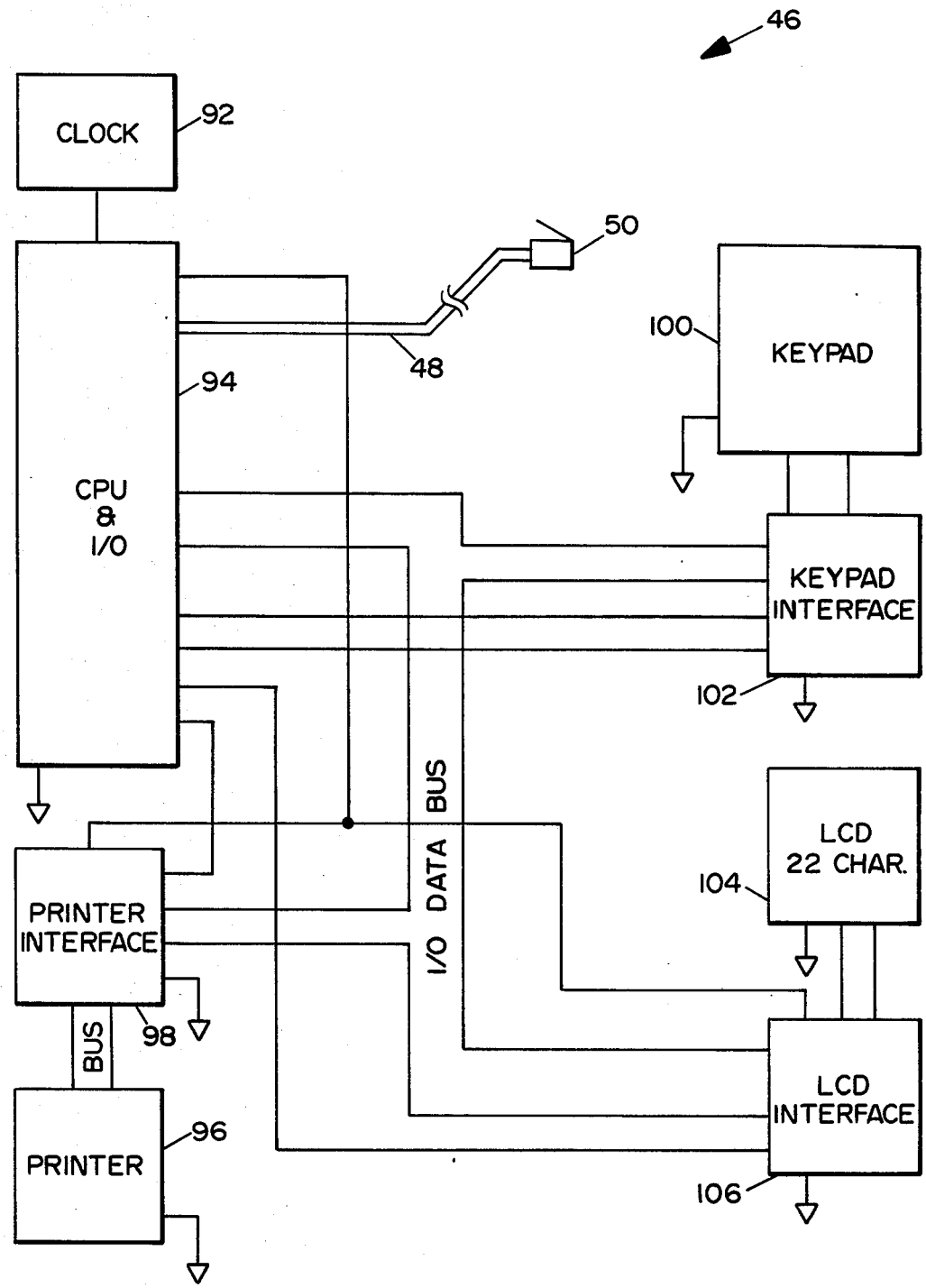
FIG. 3 illustrates a block diagram of the external controller for the drug dispenser.

FIG. 3 illustrates a block diagram of the external controller 46 for the drug dispenser 12 and includes clock 92 connected to a CPU 94. A printer 96 connects through a printer interface 98 to CPU 94 and a key pad of 16×1 100 connects through a key pad interface 102 to CPU 94. An LCD display 104 connects through an interface 106 to the CPU 94 and can be a 22-character alphanumeric multiplexed display.

Figure 4A:
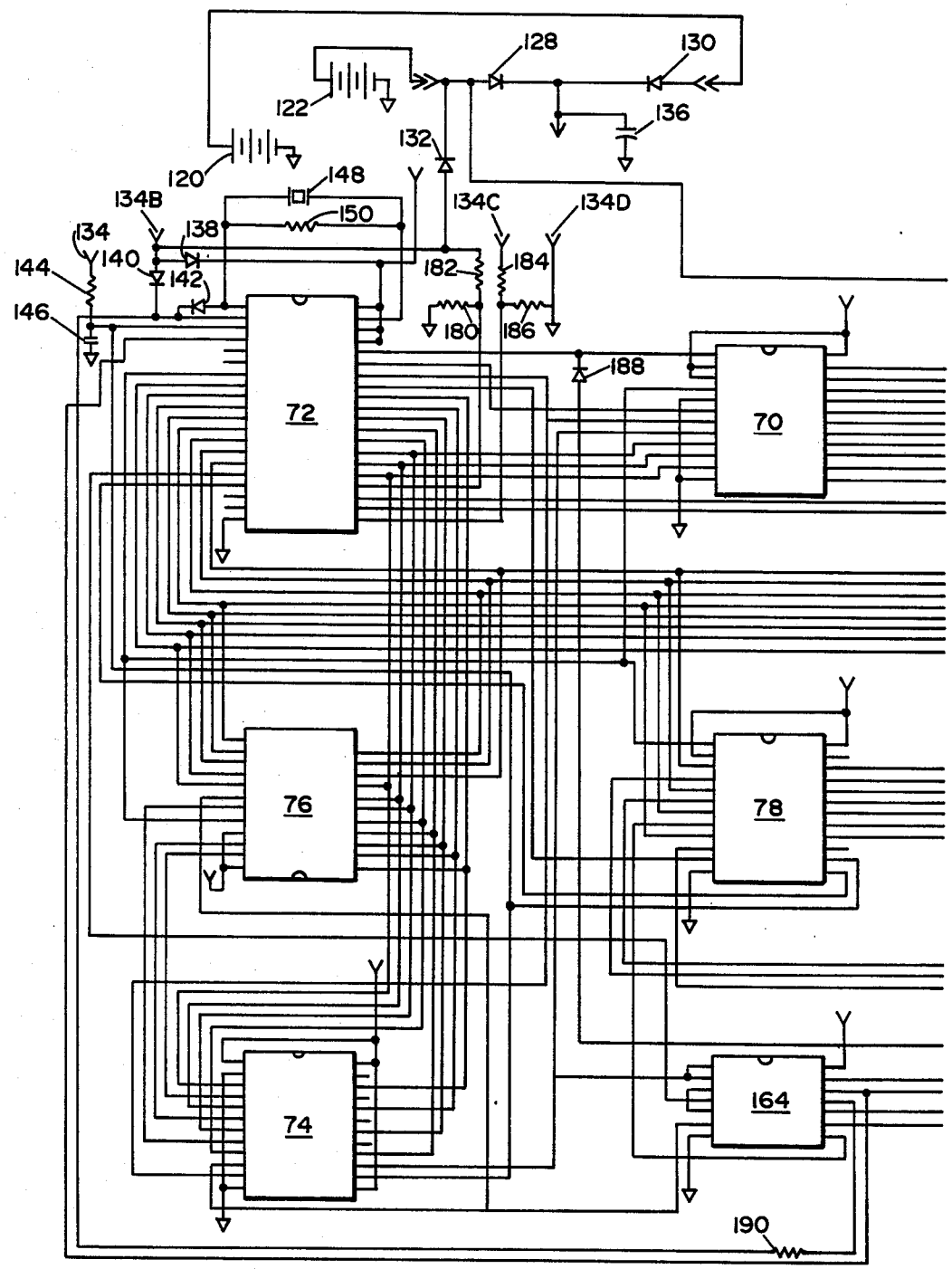
FIGS. 4A and 4B illustrate an electrical schematic diagram of the drug dispenser; and, FIGS. 5A and 5B illustrate an electrical schematic diagram of the external controller.
Figure 4B:
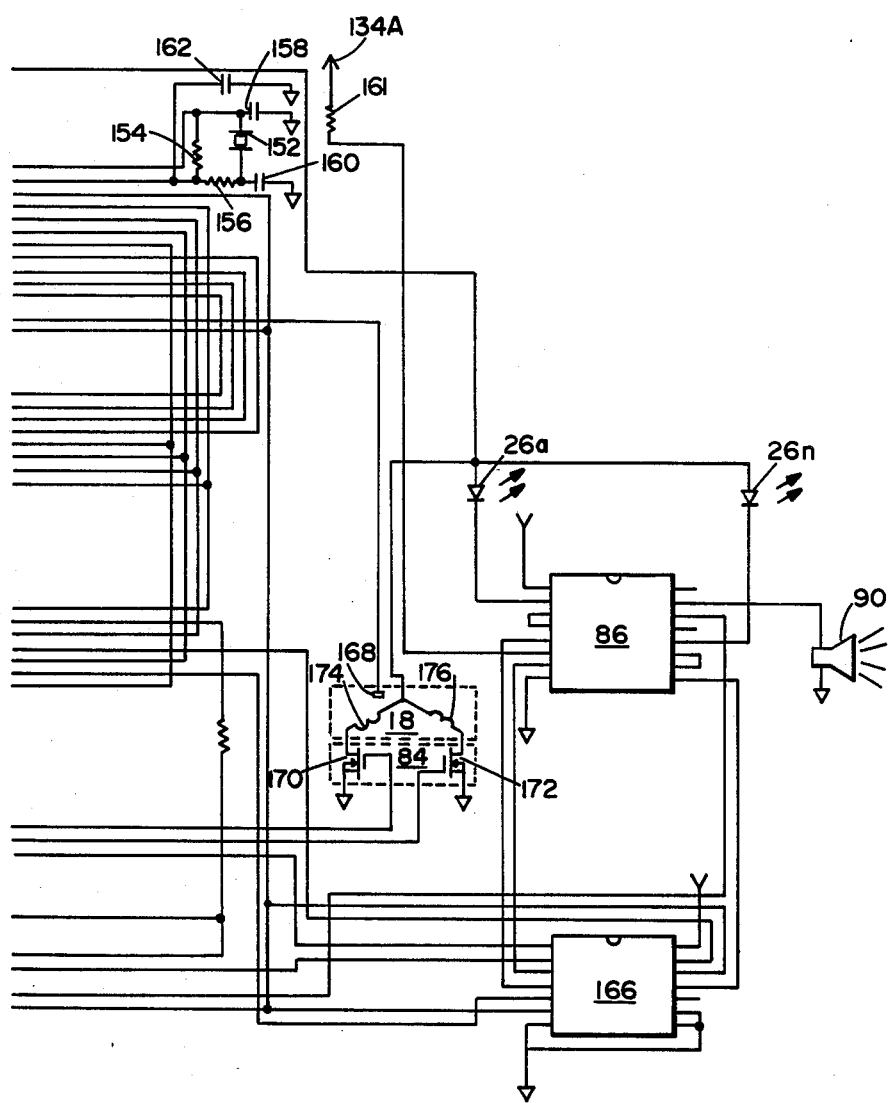

FIGS. 4A and 4B illustrate the electrical schematic diagram of the drug dispenser 12. The power source can comprise a backup first lithium power source 120, and a second nickel cadmium rechargeable battery power source 122. (The nicad battery 122 can include an external rechargeable source 224, the rechargeable source suitable for AC line current. Switching diodes 128 and 130 prevent the batteries from discharging into each other. A recharging supply isolation diode 132 ties into a jack 27 or 50 via 134B which also accepts current from the external controller 38. Jack 27 or 50 handles the heavier charging currents for recharging of the battery 122. A filter capacitor 136 removes any noise. The diode 138 supplies power to the system when the controller is plugged in. Diode 140 provides the control signal for the CPU to start whenever the external controller 38 is plugged into the jack 27 or 50. The same line is also controlled by software via the input/output chip 78 and the CPU Q-line 72. The three power supply outputs can be switched accordingly to the drug dispenser.

The clock 70 provides a power-down mode which is programed for the clock to put out an alarm, or in the alternative to be interrogated by the CPU 72 to determine subsequent activity based on a time interval. The CPU 72 operates with a 480Khz oscillator including crystal 148 and components 142–150. The clock 70 runs at 32.768 Khz including a crystal 152 and components 152–162, by way of example. In a preferred embodiment the oscillator for the clock 70 runs continuously while the oscillator for the CPU 72 runs only when the CPU is processing instructions. Otherwise, the oscillator for the CPU 72 is shut off by I/O 78. Of course in an alternative embodiment, the oscillator could run continuously. The oscillator frequency of the CPU 72 provides that the software simulates a UART at 300 baud to send and receive from a terminal. A 2K×8 EPROM 76 connects to the CPU 1805. Memory addressing is accorded through the CPU 72 and an 8-bit address decoder 74 configured as an output port. This latches the high order of 8 bits to the 16-bit address buss. These particular digital rates are by way of example and illustration only, and not to be construed as limiting of the invention. Input/output 78 supplies controlling signals to the CPU 72 for turning off the oscillator, for turning on and driving the motor 18, and to the LED indicators 26a–26n. Acoustic alarm 90 indicates a major fault condition such as battery needs recharging, the drug reservoir needs refilling, or the motor has stopped. The acoustical alert is driven through LiCl cell 120 so that the alert always functions. Integrated circuit 164 provides inversions of signals for memory address, and for turning on and off the CPU 72 oscillator. Logic inverter 166 supplies the inversion of logic signals for the indicator devices through the buffer chip 86. The lower eight bits of address are handled by the CPU 72 directly. In order, the flashing scheme for the CPU 72 begins at an instruction site with the CPU 72 flashing on the address buss the high order eight bits first with a latching control signal TPA and then places the lower order of eight bits on the bus for the remainder of the instruction cycle. The actual instruction is executed by an additional control signal called TPB, the only other input to the CPU being the pump sensor line 168 which is a switch which is actuated every time the pump goes around. This provides that the CPU 72 counts for computing the amount of drug dispensed as well as counting the dispensing per interval.

The pump 18 includes the motor buffer 84 of two transistors 170 and 172 driving coils 174 and 176 propelling a shaft 178 of FIG. 1 in a stepping fashion through a permanent magnet reciprocating and driving a shaft. The pump motor 18 through the sensing switch 168 which can constitute a spring-actuated microswitch or the like which is struck by the shaft of the motor driving a plurality of spring-actuated rollers about tubing provides for counting and subsequent computing of the dispensing of the amount of drug. The motor in this particular instance comprises a stepping motor through the reciprocating permanent magnet driving against a gear rod propelling circularly a plurality such as four, by way of example and for purposes of illustration only, spring-biased rollers rolling about flat tubing which connects to an input tube and an output tube. The input tube can connect either to an I.V. bottle or to an ampul of drug such as that of a predetermined quantity.

Figure 5B:
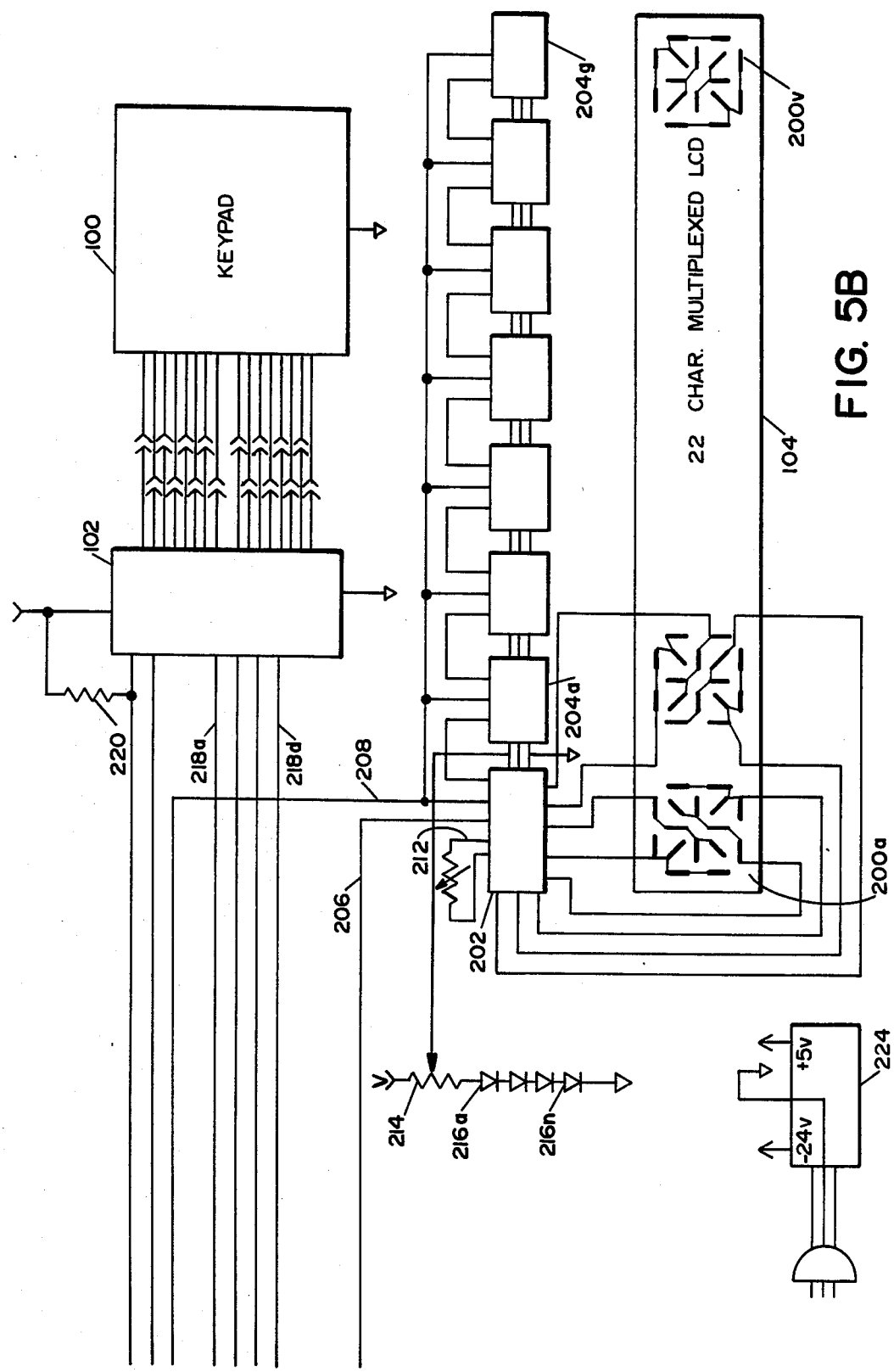

FIGS. 5A and 5B illustrate the electrical circuit diagram of the external controller 38. The display 104 is a 22-character multiplexed LCD display utilizing 16 bits of information for each character of the 16 components forming each character of the display. The display includes characters 200a–200v. The display 104 and characters are driven by an LCD master driver 202 and slaves 204a–204g. The slave drivers take the serial data dumped into the master driver and shift the data on down on the multiple-character multiplexed LCD display. The shift occurs on being filled with 48 bits of information from the serial data feed line 206 and as timed by the clock line 208. Each 16 elements of the LCD characters 200a–200v require a shift timing in 16 bits for each of the characters. The variable resistor 212 provides for timing of the master driver. Variable resistor 214 and diodes 216a–216n provide for a temperature compensated voltage regulated supply for the display 104. The adjustment of voltage is critical, due to the multiplexing of the LCD. The key pad 100 is a 16×1 pad through the key pad interface 102 with address select lines 218a–218d to the CPU 94. The resistor 220 provides for voltage for "Key Selected" direction. An acoustic alert 222 for the key pad 100 provides for auditory feedback upon digitory interaction between a pressing by the finger and the key pad. Appropriate interconnections are provided between the CPU 94 and the printer 96 including the interface I/O line. The master driver 202 connects to the CPU 94. The key pad 100 connects through the interface 102 into the CPU 94. An AC power source 224 provides power and charges the nicad battery power source.

MODE OF OPERATION

The external controller 38 is based upon a CPU board 94 such as an RCA-1802 processor and including peripheral site for adding external components, necessary I/O, 4K of RAM, and EPROM. The CPU 94 controls the printer 96, the key pad 100, and the LCD character display 104. The key pad 100 includes a key pad interface 102 such as a 16×1 matrix which converts a 16-line multiplex to a one-line via an address bus. The CPU 96 I/O configuration sets the address and then strobes with a line in the naught condition providing the signal necessary to see which key is being strobed. The comment of that is then fed back to a flag input on the CPU 94. The liquid crystal display 104 and interface 204a–204n can be a suitable 22-character display driven by a 4×4 matrix bus. The interface chip can be driven from the common I/O bus from the CPU 94 and the N5 output strobe. The printer 96 and printer interface 98 is driven on a 1–8 data buss and appropriate handshaking signals by the printer interface and has a 20-character left-to-right electrostatic printer system, by way of example and for purposes of illustration only. The printer interface is also driven from the common I/O bus, and is strobed by the TO-P output strobe from the CPU 94.

The external controller 38 is designed to be user prompted by the controller to allow the user to select the mode in which it is desired to have the drug dispensing pump operate. The printer 96 prints out all of the activity, providing the user a hard-copy record, which is particularly important for Medicare and Social Security reasons.

The external controller 38 connects to the drug dispenser 12 with a standard modular RJ11C jack 50 and standard telephone cord system. The cable and jacks are wired identically to that of the telephone cord so that in the event of cable failure any telephone cord could be substituted. Once an algorithm is selected the subsequent programming is then sent out to the CPU in the drug dispenser 12 for programming at the algorithm as selected by the user.

The user is prompted by both the LCD display 104 and the printer 96 in inputting parameters to the system 10.

The following parameters are programmed through the external controller 38 into the drug dispenser 12: (1) patient hospital identification, (2) patient name, (3) drug dispenser number (drug dispenser 12), (4) date, (5) time, (6) drug identification number, (7) drug dispensing algorithm, (8) dosage level, and (9) frequency of dosage.

The drug dispensing algorithm 7 can be those algorithms stored in CPU 94 as programmed into the CPU, and can correspond to programs in the CPU or programs which are dumped into the CPU from a second programming source such as an external microcomputer or the like. The algorithms can correspond to algorithms for treating certain types of diseases with certain dosage levels over certain predetermined time intervals, can correspond to general algorithms for specific drugs in dispensing predetermined amounts of drug over predetermined intervals for a specific weight or age patient, and can also correspond to algorithms inputted in from a microcomputer external to that of the external controller 38.

The pump 18 of the drug dispenser 12 operates primarily in three modes. The pump can operate in a continuous flow mode which requires that a program selected algorithm over a period of time dispenses a total volume amount and the drug dispenser 12 ceases such dispensing once that total amount has been dispensed. Monitoring of the dispensed amount is done by the detector line 168. The algorithm also decides on the rate that the drug is dispensed over that predetermined time interval. The second mode is a bolus per time interval mode; that is, so much drug over a predetermined time interval at a particular time interval. The third mode of configuration is based on a 24-hour clock arrangement; that is, such as dispensing so much drug three, four, etc. times daily. The specific times can also be programmed in for dispens- ing.

Of course, other modes of drug dispensing are selectable, which is dependent either on stored algorithms in the CPU of the external controller which are subsequently programmed into the CPU of the drug dispenser, programs which are programmed into the CPU 94 through the key pad 100, or programs which are dumped into the CPU 94 by an external microcomputer, for subsequent programming into the CPU 72.

Assignee as well as others has programs which can be stored on diskette, audio tape, or on other storage memories for subsequent dumping into the CPU 94 or directly into the CPU 72 for dispensing of drugs. The programs are only limited by the parameters of the drug, of the interval, and the specifics of the patient such as size, weight, age, and physical abnormalities or allergies or other human factors which are to be determined.

The drug dispenser 12 includes commonly available "over-the-counter" integrated circuits including the microprocessor, such as an RCA 1805, a CMOS ultraviolet EPROM, 8-bit input/output ports, real-time clock, dual input quad-nand gates, CMOS hex-inverting buffers, VMOS N-channel FETs, light-emitting diodes, Schottky diodes, acoustic transducer and tuning fork oscillators. These components are readily available and can be utilized accordingly or interchanged by like components.

For the external controller 38, the CPU is an RCA COSMAC microboard computer and includes an electrostatic printer and interface, a CMOS analog multiplexer, membrane switch, master and slave multiplexed LCD drivers, alphanumeric liquid crystal display, and an acoustic transducer. This acoustic transducer for the external controller as well as for the drug dispenser can operate at approximately 2.7 Khz or the like frequency.

The drug being dispensed can be that from an ampule of such a size to fit into the drug dispenser housing 12 at the ampule location 16 for accommodating such a size of ampule or from an external drug reservoir such as an I.V. bottle or the like. With the introduction of drug dispensing, drug companies will be providing ampules of drugs so packaged into containers for either connection to a drug-dispensing pump motor tube or for ampules including the drug in an ampule 16, drug dispensing motor tube 192, and tube 30 with needle for the patient all in one sterile package. Consequently, such a drug would be provided in the ampule and include the necessary sterile tubing from the ampule through the motor pump, and to the patient, which could be easily positioned into the drug dispenser housing and components 12 as required by either a nurse, medical technician, or other medical personnel. The drug dispensing system 10 lends itself to specific packaging requirements by the drug companies and only requires the accommodation of a specific pump motor tube which is readily available through medical extrusion companies and the like. Of course, the drug dispensing housing 12 can accommodate any drug of a liquid nature through the motor pump tubing from any type of a container to a tube to the patient's arm. The only specific requirement is that the drug be fed into the motor input tube for subsequent feeding through the output tube 30 to the patient about the adjacent perimeter of the shaft.

Various modifications can be made to the present invention without departing from the apparent scope thereof. The display could also be LED, video, or the like.

I claim:

1. Drug dispensing system comprising:
   a. means for external programming control including a first CPU including a first memory means including a plurality of drug dispensing algorithms stored therein, key pad input means connected to said first memory means for selecting one of said algorithms and inputting parameters for said algorithm therein, display for self-prompting as well as viewing-selected input, printer means providing hard copy; and,
   b. means for drug pump dispensing including a second CPU including second memory means for storing an algorithm with selected parameters inputted only from said external programming control means, discrete real-time clock and calendar means for controlling predetermined levels of drug dispensing and connected to said second CPU, drug reservoir means, pump means connected to said drug reservoir means for pumping a drug through a tube to a patient, motor means for said pump means connected to said second memory means for driving said pump means, and visual indicator means indicating status of said pump means.

2. System of claim 1 wherein said external programming control means includes means for inputting parameters including patient identification number, patient name, drug dispenser number, date, time, drug identification number, drug dispensing algorithm, dosage level, and frequency of dosage.

3. System of claim 1 wherein said external programming control includes auditory feedback means for providing indication of digital depression of said key pad input means.

4. System of claim 1 wherein said display comprising an alphanumeric multiplexed character LCD display shifting from left to right.

5. System of claim 4 wherein said character display comprises 22 characters.

6. System of claim 5 wherein each character comprises 16 elements.

7. System of claim 1 wherein said printer means provides hard copy.

8. System of claim 1 wherein said printer means provides electrostatic hard copy.

9. System of claim 1 wherein said second memory means includes means for storing amount of drug dispensed.

10. System of claim 1 wherein said second memory means includes backup emergency power source means.

11. System of claim 1 wherein said second memory means includes means for dispensing drug from either an ampule or an I.V. bottle.

12. System of claim 1 wherein said display comprises a video display.

13. System of claim 1 comprising external computer means for storing algorithms and connected to said second CPU.

14. System of claim 1 comprising means for programming said second CPU in three dispensing modes of a continuous flow mode, a bolus per time interval mode, and a 24-hour clock mode.

15. System of claim 1 comprising an I/O means connected to said second CPU.

16. System of claim 15 wherein said I/O means is connected to an external modem.

17. System of claim 16 including means for connecting said external modem to a telephone line.

18. System of claim 15 wherein said I/O means includes means for receiving external interrogation by a computer means and external programming by a computer means.

19. System of claim 15 comprising external programming source means connected to said I/O means.

20. System of claim 1 wherein said means for drug pump dispensing is ambulatory.

21. System of claim 1 comprising internal rechargeable power source means powering said drug dispensing means.

22. System of claim 1 wherein said means for drug pump dispensing functions independently of alarm functions.

23. System of claim 1 wherein said algorithms provide for drug dosages over real time.

24. System of claim 1 wherein said second CPU operates as a UART at 300 baud.

25. System of claim 1 wherein each said algorithm includes dosage levels and frequency of dosages.

26. Drug dispensing system comprising:
   a. means for external programming control including a first CPU including a first memory, said first memory including a plurality of drug dispensing algorithms stored therein, key pad input means connected to said first memory for selecting one of said algorithms and inputting parameters for said algorithm therein, display for self prompting as well as viewing selected input connected to said first CPU and a printer means providing hard copy connected to said CPU; and,
   b. means for drug pump dispensing including a second CPU including a second memory for storing an algorithm and selected parameters inputted only from said external control means, discrete real-time clock and calendar means for controlling predetermined levels of drug dispensing and connected to said second CPU, drug reservoir means, pump means connected to said drug reservoir means for pumping a drug through a tube to a patient, motor means for said pump means connected to said second memory for driving said pump means, said pump means powered by said second CPU in a continuous flow mode, bolus per time interval mode, and a 24-hour clock mode including dosage levels and frequency of dosages, and visual indicator means connected to said second CPU and indicating status of said pump means.

27. Drug dispensing system comprising CPU means including memory means for storing drug dispensing algorithms with predetermined parameters, drug reservoir means, pump means connected to said drug reservoir means for pumping said drug through a tube to a patient, motor means for said pump means connected to said CPU means for driving said pump means, switch means mechanically coupled to said pump means for generating a pump status signal in response to operation of said pump means, means connecting said switch means to said CPU means to convey said status signal to said CPU means, said pump means powered by said CPU means in accordance with selected predetermined parameters in said memory means of said CPU means in a continuous flow mode, bolus per time interval mode, and a 24-hour clock mode including dosage level and frequency of dosage, and visual indicator connected to said CPU means and responsive to said pump status signal for indicating status of said pump means.

* * * * *